United States Patent [19]

Nakagawa et al.

[11] Patent Number: 4,974,774
[45] Date of Patent: * Dec. 4, 1990

[54] MEDICAL APPLIANCE DRIVING APPARATUS

[75] Inventors: Masakazu Nakagawa, Tokyo; Sanshiro Takamiya, Nagoya, both of Japan

[73] Assignee: Aisin Seiki Kabushiki Kaisha, Aichi, Japan

[*] Notice: The portion of the term of this patent subsequent to May 23, 2006 has been disclaimed.

[21] Appl. No.: 229,803

[22] Filed: Aug. 4, 1988

Related U.S. Application Data

[63] Continuation of Ser. No. 30,651, Mar. 26, 1987, abandoned.

[30] Foreign Application Priority Data

Mar. 26, 1986 [JP] Japan .................. 61-068007

[51] Int. Cl.$^5$ .............................................. A61M 1/02
[52] U.S. Cl. .......................................... 600/18; 623/3
[58] Field of Search ................................... 600/16–18; 623/3; 604/96–98

[56] References Cited

U.S. PATENT DOCUMENTS

| | | | |
|---|---|---|---|
| 3,698,381 | 10/1972 | Federico et al. | 128/1 D |
| 3,720,199 | 3/1973 | Rishton et al. | 604/98 |
| 3,755,825 | 9/1973 | DeBakey et al. | 623/3 |
| 4,016,871 | 4/1977 | Schiff | 623/3 |
| 4,162,543 | 7/1979 | Shumakov et al. | 128/1 D |
| 4,548,550 | 10/1985 | Tsuji . | |
| 4,556,997 | 12/1985 | Takimiya . | |
| 4,583,525 | 4/1986 | Suzuki et al. | 623/3 |
| 4,597,381 | 7/1986 | Oumi et al. | 128/1 D |
| 4,600,015 | 7/1986 | Evans et al. | 604/97 |
| 4,648,385 | 3/1987 | Oumi et al. | 128/1 D |
| 4,662,358 | 5/1987 | Farrar et al. | 623/3 |
| 4,787,368 | 11/1988 | Kageyama | 600/18 |
| 4,796,606 | 1/1989 | Mushika | 600/18 |
| 4,832,005 | 5/1989 | Takamiya et al. | 600/18 |

FOREIGN PATENT DOCUMENTS

| | | |
|---|---|---|
| 59-177062 | 10/1984 | Japan . |
| 59-206698 | 11/1984 | Japan . |
| 59-206699 | 11/1984 | Japan . |
| 59-207158 | 11/1984 | Japan . |
| 60-106462 | 6/1985 | Japan . |

Primary Examiner—Stephen C. Pellegrino
Assistant Examiner—Ralph Lewis
Attorney, Agent, or Firm—Sughrue, Mion, Zinn, Macpeak & Seas

[57] ABSTRACT

A medical appliance driving apparatus includes positive and negative pressure sources and an isolator having an input chamber and an output chamber which are defined by a movable membrane. A first switching valve is connected to the positive pressure source and has its output side connected to the input chamber. A second switching valve is connected to the negative pressure source and has its input side connected to the input chamber. A solenoid valve is also connected to the input chamber. A microcomputer supplies the isolator with a positive or negative pressure by controlling the operation of the first or second switching valve, and after opening the first switching valve, closes it and controls the operation of the solenoid valve so as to adjust the pressure in the input chamber to a predetermined positive pressure value. A positive pressure is supplied to the input chamber of the isolator by opening the first switching valve, thus moving the movable membrane in a direction in which the medical appliance is expanded. After the medical appliance has sufficiently been expanded, the supply of positive pressure is cut off, and the operation of the solenoid valve is controlled so that the pressure in the input chamber is adjusted to a predetermined positive pressure value. Accordingly, when a negative pressure is supplied by opening the second switching valve at the subsequent timing, the negative pressure can be made to act even more effectively. Thus, it is possible to quicken the movement of the medical appliance when contracted.

3 Claims, 6 Drawing Sheets

MEDICAL APPLIANCE DRIVING APPARATUS

This is a continuation of application Ser. No. 030,651, filed Mar. 26, 1987, now abandoned.

BACKGROUND OF THE INVENTION

1. Field of the Invention

The present invention relates to a medical appliance driving apparatus designed to expand and contract a medical appliance such as an artifial heart pump or an intraaorta balloon pump by alternately supplying positive and negative pressures thereto. More particularly, the present invention pertains to an apparatus for driving an intraaorta balloon pump.

2. Description of the Related Art

Medical appliance driving apparatuses are demanded to increase the speed of expansion and contraction of the associated medical appliances. It is preferable, in order to meet such requirements, to make steep the rise (or fall) of the pressure supplied to the medical appliances. For this reason, one type of driving apparatus employs an accumulator to prevent variations in pressure. However, it is necessary to considerably increase the capacity of the accumulator in order to absorb a rise or lowering in pressure produced in the accumulator when the state of the medical appliance is changed from expansion to contraction or vice versa. Accordingly, it is difficult to reduce the overall size of the driving apparatus.

There is another type of medical appliance driving apparatus wherein a solenoid valve is disposed in parallel to a pressure regulating valve and a pressure from a pressure source such as a compressor or a vacuum pump is directly supplied to the medical appliance by controlling the solenoid valve so as to be opened and closed at a predetermined timing, thereby making compensation for the rise of pressure supplied to the medical appliance.

For example, a driving apparatus disclosed in U.S. Pat. No. 4,556,997 is arranged such that, while a negative pressure is being supplied to a medical appliance, a positive pressure is directly led from a compressor through a solenoid valve and kept higher than a set pressure regulated by a pressure regulating valve to thereby compensate for the rise of pressure when a positive pressure is supplied to the medical appliance.

Driving apparatuses disclosed in U.S. Pat. No. 4,548,550 are arranged such that, when a positive pressure is supplied to a medical appliance, a positive pressure from a compressor is directly supplied through a solenoid valve for a predetermined period of time to thereby compensate for the rise of pressure supplied to the medical appliance.

Driving apparatuses disclosed in U.S. Pat. No. 4,548,550 are provided with an auxiliary accumulator for accumulating a positive pressure from a compressor in addition to an accumulator for accumulating a regulated pressure, and when the regulated pressure is supplied to the medical appliance, the pressure accumulated in the auxiliary accumulator is supplied together with said regulated pressure to thereby make compensation for the rise of pressure supplied to the medical appliance.

A driving apparatus disclosed in U.S. Pat. No. 4,648,385 is arranged such that, when a positive pressure is supplied to a medical appliance, a positive pressure from a compressor is directly supplied through a solenoid valve to thereby compensate for the rise of pressure supplied to the medical appliance, and when the pressure in the medical appliance reaches a predetermined value, the solenoid valve is closed.

In all of these driving apparatuses, a pressure from a pressure source is directly led to a medical appliance in order to compensate for the rise (or fall) of pressure supplied to the medical appliance. Accordingly, when the medical appliance is to be expanded, a positive pressure fluid is needed to compensate for a negative pressure in the pipe line or the like, whereas, when the medical appliance is to be contracted, a negative pressure fluid is needed to compensate for a positive pressure in the pipe line. For this reason, it has heretofore been unavoidable that the rise of pressure at the time of switching the state of the medical appliance from expansion to contraction and vice versa is somewhat slow.

SUMMARY OF THE INVENTION

In view of the above-described circumstances, it is a primary object of the present invention to provide a medical appliance driving apparatus which is so designed that said rise (or fall) of pressure is as steep as possible.

To this end, the present invention provides a medical appliance driving apparatus comprising: positive pressure supply means for supplying a positive pressure; negative pressure supply means for supplying a negative pressure; isolator means having an input chamber and an output chamber which are defined by a movable membrane; first switching valve means connected to the positive pressure supply means and having its output side connected to the input chamber of the isolator means; second switching valve means connected to the negative pressure supply means and having its input side connected to the input chamber of the isolator means; valve means connected to the input chamber of the isolator means; pressure deteting means for detecting the pressure in the input chamber of the isolator means; and electronic control means which supplies the isolator means with a positive or negative pressure by controlling the operation of the first or second switching valve means and which, after opening the first switching valve means, closes it and controls the operation of the valve means so as to adjust the pressure in the input chamber of the isolator means to a predetermined positive pressure value.

According to the above-described arrangement, a positive pressure is supplied to the input chamber of the isolator means by opening the first switching valve means, thus moving the movable membrane in a direction in which the medical appliance is expanded. After the medical appliance has sufficiently been expanded, the supply of positive pressure is cut off, and the operation of the valve means is controlled so that the pressure in the input chamber is adjusted to a predetermined positive pressure value. More specifically, after the movable membrane has been moved to a predetermined position, the positive pressure is lowered to a level at which the movable membrane can satisfactorily be held at said position. Accordingly, when a negative pressure is supplied by opening the second switching valve means at the subsequent timing, the negative pressure can be made to act even more effectively. Thus, it is possible to quicken the movement of the medical appliance when contracted.

The driving apparatus according to the present invention further has position detecting means for detecting the fact that the movable membrane has moved to a predetermined position. When the movable membrane has reached the predetermined position, the first switching valve means is closed and the operation of the valve means is controlled to adjust the pressure in the input chamber. Thus, the fact that the medical appliance has sufficiently been expanded can be detected on the basis of the position of the movable membrane.

In addition, when the medical appliance is expanded, it is possible to supply a pressure medium having a pressure which is higher than that in the case of the conventional driving apparatuses. This is because, after the movable membrane has moved to a predetermined position, the pressure is lowered to a level at which the movable membrane can satisfactorily be held at said position, whereby it is possible to prevent application of an excessively high pressure to the medical appliance. Accordingly, it is possible to quicken the movement of the medical appliance when expanded.

The driving apparatus according to the present invention further has an arrangement for allowing the input chamber to communicate with the positive pressure source, and the electronic control means activates the switching valve means to negative pressure regulating means side at a predetermined timing, and, activates the valve means to the positive pressure source side when the movable membrane has moved to a second predetermined position to set the pressure in the input chamber at a second predetermined pressure value which is greater than the value of pressure regulated by the negative pressure regulating means.

By virtue of this arrangement, the movable membrane is moved in a direction in which the medical appliance is contracted by activating the switching valve means to the negative pressure regulating means side. After the movable membrane has reached the predetermined position, the pressure in the input chamber is set at the predetermined pressure. More specifically, after the movable membrane has reached the predetermined position, the negative pressure is raised to a level at which the movable membrane can satifactorily be held at said position. Accordingly, when a positive pressure is supplied by switching the switching valve means at the subsequent timing, the positive pressure can be made to act even more effectively. In other words, it is possible to quicken the movement of the medical appliance when expanded.

In this case also, when the medical appliance is to be contracted, it is possible to supply a pressure medium which has a lower pressure than that in the case of the conventional driving apparatuses. Accordingly, it is possible to quicken the movement of the medical appliance when contracted.

The above and other objects, features and advantages of the present invention will become clear from the following description of the preferred embodiment thereof taken in conjunction with the accompanying drawings.

DESCRIPTION OF THE PREFERRED EMBODIMENT

One embodiment of the present invention will be described hereinunder in detail with reference to the accompanying drawings.

Figure 1:
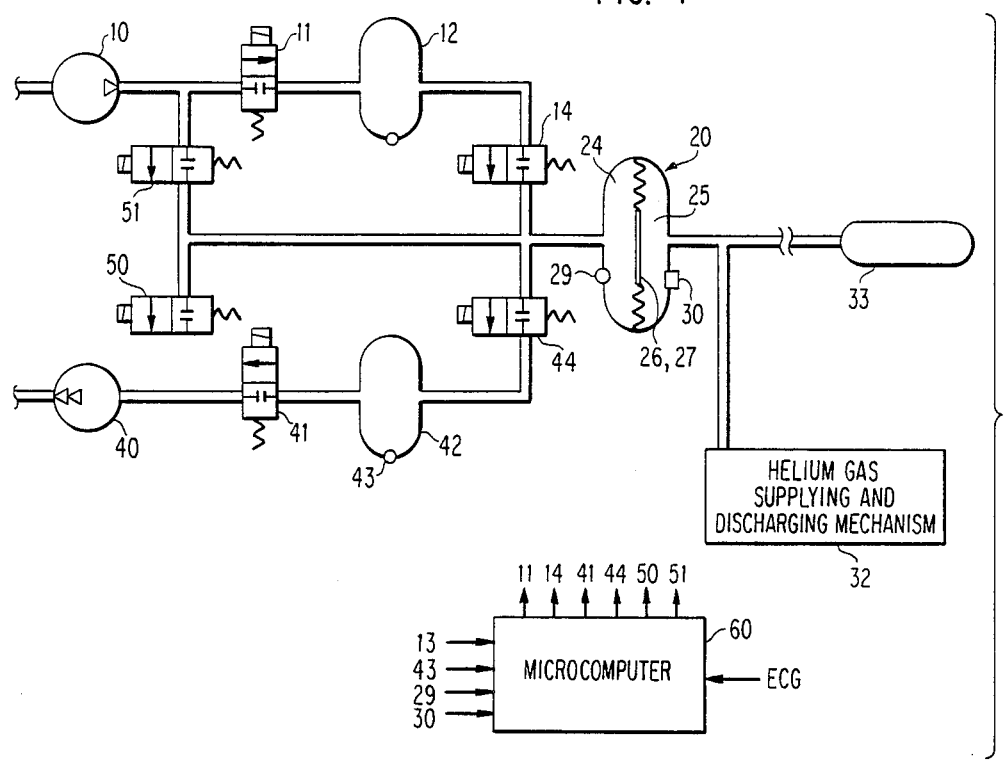
FIG. 1 is a block diagram of one embodiment of the medical appliance driving apparatus according to the present invention.

Referring first to FIG. 1, which is a block diagram of a medical appliance driving apparatus according to the present invention, the output side of a compressor 10 which serves as a positive pressure source is connected to a pressure regulating valve 11 the output side of which is, in turn, connected to a tank 12. A pressure sensor 13 for detecting pressure is disposed on the tank 12.

The output side of the tank 12 is connected to a solenoid valve 14 which serves as switching valve means. The output side of the solenoid valve 14 is connected to an isolator 20 which serves as isolator means. The isolator 20 changes a medium for driving a medical appliance from air to a gas such as helium. Thus, a driving medium is made safe for living organisms.

Figure 2:
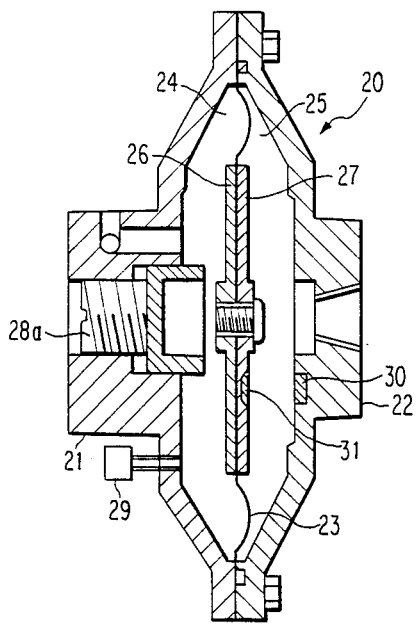
FIG. 2 is a sectional view of the isolator means shown in FIG. 1.

Referring next to FIG. 2, which shows the isolator 20 in detail, the interior of the isolator 20 is divided into an input chamber 24 and an output chamber 25 by means of a diaphragm 23 which is clamped between housings 21 and 22. Plates 26 and 27 are secured to both sides, respectively, of the central portion of the diaphragm 23. The diaphragm 23 and the plates 26, 27 define in combination a movable membrane. A limiting member 28 for limiting the amount of movement of the plate 26 is secured to the central portion of the housing 21. The limiting member 28 is in thread engagement with the housing 21 by means of a screw 28a. When turned, the limiting member 28 is moved sideways as viewed in the figure. When the limiting member 28 is moved leftward, the range within which the plates 26 and 27 can move is enlarged, whereas, when the limiting member 28 is moved rightward, said movable range is decreased.

A pressure sensor 29 which serves as pressure detecting means is disposed on the side of the housing 21 which is closer to the input chamber 24. A Hall element sensor 30 which serves as position detecting means for detecting the position of the plates 26 and 27 is disposed on the side of the housing 22 which is closer to the output chamber 25. A magnet 31 is disposed on the plate 27 so that the magnet 31 faces the Hall element sensor 30. Since the Hall element sensor 30 is capable of obtaining an output proportional to the magnitude of an external magnetic field, it is possible to detect of the plate 27 on the basis of the output of the sensor 30.

Referring back to FIG. 1, the output chamber 25 of the isolator 20 is connected to a helium gas supplying and discharging mechanism 32 and an intraaorta balloon pump 33 which defines a medical appliance in this embodiment. The helium gas supplying and discharging mechanism 32 serves to maintain the pressure of helium gas within the isolator 20 and the balloon pump 33 at a constant level.

The output of a vacuum pump 40 which serves as a negative pressure source is connected to a pressure regulating valve 41 the output side of which is, in turn, connected to a tank 42. A pressure sensor 43 for detecting pressure is disposed on the tank 42.

The output side of the tank 42 is connected to a solenoid valve 44 which serves as switching valve means.

The output side of the solenoid valve 44 is connected to the input chamber 24 of the isolator 20.

The input chamber 24 of the isolator 20 is connected to the input side of a solenoid valve 50 which serves as valve means. The output side of the solenoid valve 50 is opened to the atmosphere. Further, the input chamber 24 of the isolator 20 is connected to the input side of a solenoid valve 51 which serves as valve means. The output side of the solenoid valve 51 is connected to the output side of the compressor 10.

To the input side of a microcomputer 60 which serves as electronic control means are connected the pressure sensors 13, 43 and 29 and the Hall element sensor 30, whereas, to the output side of the microcomputer 60 are connected the pressure regulating valves 11, 41 and the solenoid valves 14, 44, 50 and 51.

The operation of the microcomputer 60 will next be explained with reference to flow charts shown in FIGS. 3, 4, 5 and 6.

Figure 3:
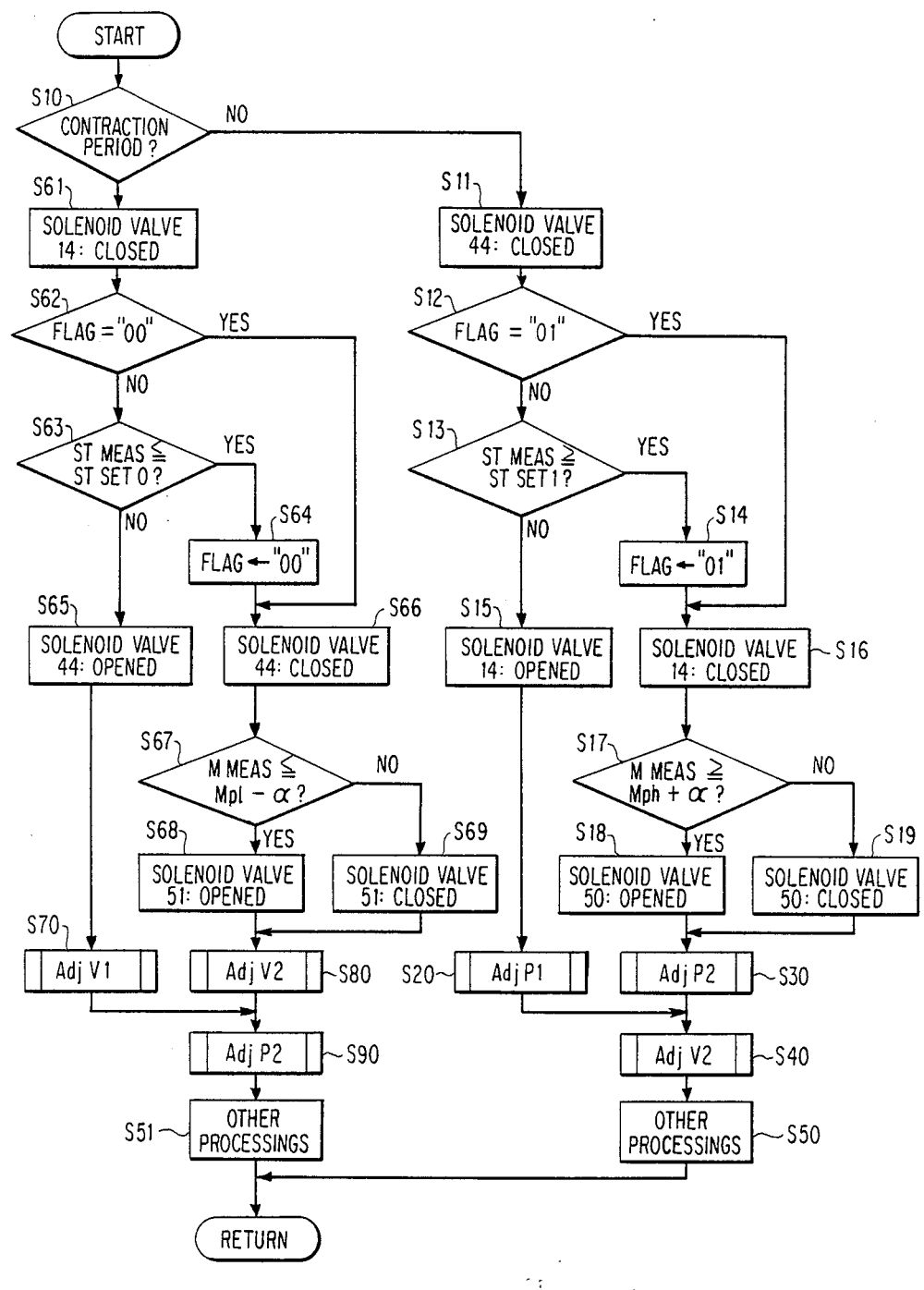
FIGS. 3, 4, 5, 6 and 7 are flow charts showing the operation of the embodiment.
Figure 4:
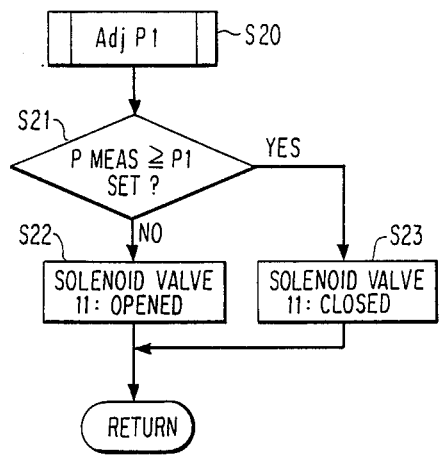
Figure 5:
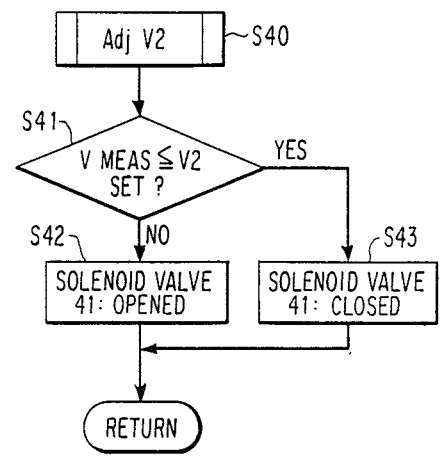
Figure 6:
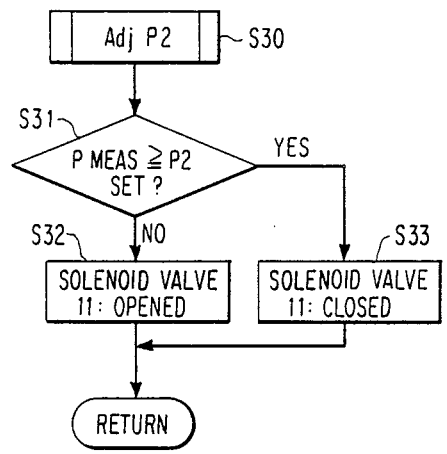

FIG. 3 shows control which is executed according to the main routine. A judgement is made in Step S10 as to whether or not the balloon pump 33 is during the contraction period. The contraction period of the balloon pump 33 is determined as follows. For example, the microcomputer 60 is externally supplied with an electrocardiogram (ECG) signal and/or a blood pressure signal concerning a living organism under treatment to perform calculation in order to obtain contraction and expansion timing which is appropriate to a particular condition of the living organism on the basis of the input data. Description of the calculation and the like is omitted herein.

When the balloon pump 33 is judged to be during the expansion period in Step S10, positive pressure supply control which is shown in infra Step S11 is executed. In this control, first, the solenoid valve 44 is closed in Step S11 to cut off the supply of negative pressure to the input chamber 24 of the isolator 20. Then, a judgement is made in Step S12 as to whether or not a movable membrane position flag "01" is up. This flag "01" is set in Step S14 when it is judged in Step S13 that the position STmeas of the plate 27 detected by the Hall element sensor 30 reaches a given set position STset1 during the expansion period. Since, in this state, the flag "01" is not up, the process proceeds to Step S15, in which the solenoid valve 14 is opened to supply a regulated positive pressure from the tank 12 to the input chamber 24. In consequence, the plate 27 is moved to expand the balloon pump 33.

At this time, positive pressure adjusting control AdjP1 shown in Step S20 is effected. This control is shown in the flow chart of FIG. 4. A judgement is made in Step S21 as to whether or not the tank pressure Pmeas represented by a value detected by the pressure sensor 13 disposed on the tank 12 is equal to or greater than a set positive pressure value P1set. When the pressure Pmeas is less than the set value P1set, the process proceeds to Step S22, in which the pressure regulating valve 11 is opened to introduce the pressure from the compressor 10 into the tank 12. When the pressure Pmeas reaches the set value P1set, the pressure regulating valve 11 is closed in Step S23.

Referring back to FIG. 3, negative pressure adjusting control AdjV2 is carried out in Step S40. This control is executed in order to set a negative pressure required during the subsequent contraction period in the tank 42 while the balloon pump 33 is being expanded by means of the positive pressure. The negative pressure adjusting control AdjV2 will be explained below with reference to the flow chart shown in FIG. 5. A judgement is made in Step S41 as to whether or not the tank pressure Vmeas represented by a value detected by the pressure sensor 43 disposed on the tank 42 is equal to or less than a set negative pressure value V2set. When the pressure Vmeas is greater than the set value V2set, the pressure regulating valve 41 is opened in Step S42 to introduce the pressure from the vacuum pump 40 into the tank 42. When the pressure Vmeas reaches the set value V2set, the pressure regulating valve 41 is closed in Step S43.

Referring back to FIG. 3, other processings are executed in Step S50, and the process returns.

When it is judged in Step S13 that the position STmeas of the plate 27 has reached the set position STset1 during the expansion period, the process proceeds to Step S14, in which the flag "01" is set, and the process then proceeds to Step S16, in which the solenoid valve 14 is closed to cut off the supply of positive pressure thereafter.

Steps 17, 18 and 19 constitute in combination a control flow for lowering the pressure in the input chamber 24 to a predetermined pressure value. If it is judged in Step S17 that the pressure value Mmeas detected by the pressure sensor 29 is higher than a first set pressure value Mph+α, the process proceeds to Step S18, whereas, if not, the process proceeds to Step S19. In Step 18, the solenoid valve 50 is opened to lower the pressure in the input chamber 24. This is continued until the detected pressure value Mmeas reaches the first set pressure value Mph+α. In Step S19, the solenoid valve 50 is closed to hold the pressure in the input chamber 24 at the first set pressure value.

It should be noted that, after these processings, the pressure in the tank 12 is set to a set pressure value P2set for the subsequent expansion period in Step S30. This control is effected in order to set a positive pressure required during the subsequent expansion period in the tank 12 while the balloon pump 33 is held in the expanded state. This control process will be explained below with reference to the flow chart shown in FIG. 6. A judgement is made in Step S31 as to whether or not the tank pressure Pmeas represented by a value detected by the pressure sensor 13 disposed on the tank 12 is equal to or greater than a set positive pressure value P2set. When the pressure Pmeas is less than the set value P2set, the pressure regulating valve 11 is opened in Step S32 to introduce the pressure from the compressor 10 into the tank 12. When the pressure Pmeas reaches the set value P2set, the pressure regulating valve 11 is closed in Step S33.

The control executed during the contraction period will next be explained with reference to FIG. 3.

Figure 7:
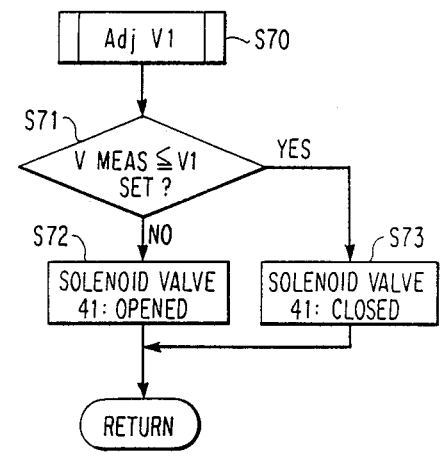

When it is judged in Step S10 that the balloon pump 33 is during the contraction period, negative pressure supply control shown in infra Step S61 is executed. In this control, first, the solenoid valve 14 is closed in Step S61 to cut off the supply of positive pressure to the input chamber 24 of the isolator 20. Then, a judgement is made in Step S62 as to whether or not a movable membrane position flag "00" is up. This flag "00" is set in Step S64 when it is judged in Step S63 that the position STmeas of the plate 27 which is detected by the Hall element sensor 30 reaches a given set position STset0 during the contraction period. Since, in this state, the flag "00" is not up, the process proceeds to Step S65, in which the solenoid valve 44 is opened to supply a regulated negative pressure to the input chamber 24. In consequence, the plate 27 is moved to contract the balloon pump 33. At this time, negative pressure adjusting control AdjV1 shown in Step S70 is effected. This control is shown in the flow chart of FIG. 7. A judgement is made in Step S71 as to whether or not the tank pressure Vmeas represented by a value detected by the pressure sensor 43 disposed on the tank 42 is equal to or less than a set negative pressure value V1set. When the pressure Vmeas is greater than the set value V1set, the process proceeds to Step S72, in which the pressure regulating valve 41 is opened to introduce the pressure from the vacuum pump 40 into the tank 42. When the pressure Vmeas reaches the set value V1set, the pressure regulating valve 41 is closed in Step S73.

Referring back to FIG. 3, the pressure in the tank 12 is set to the set value P2set for the subsequent expansion period in Step S90. This control is executed in order to set a positive pressure required during the subsequent expansion period in the tank 12 while the balloon pump 33 is being contracted. Since this is the same as the positive pressure adjusting control AdjP2 shown in FIG. 6, description thereof is omitted.

Referring back to FIG. 3, other processings are executed in Step S51, and the process returns.

When it is judged in Step S63 that the position STmeas of the plate 27 has reached the set position STset0 during the contraction period, the process proceeds to Step S64, in which the flag "00" is set, and the process then proceeds to Step S66, in which the solenoid valve 44 is closed to cut off the supply of negative pressure thereafter.

Steps S67, 68 and 69 constitute in combination a control flow for raising the pressure in the input chamber 24 to a predetermined pressure value. If it is judged in Step S67 that the pressure value Mmeas detected by the pressure sensor 29 is lower than a second set pressure value $Mpl-\alpha$, the process proceeds to Step S68, whereas, if the former is higher than the latter, the process proceeds to Step S69. In Step S68, the solenoid valve 51 is opened to raise the pressure in the input chamber 24. This is continued until the detected pressure value Mmeas reaches the second set pressure value $Mpl-\alpha$. Then, the solenoid valve 51 is closed in Step S69 to hold the pressure in the input chamber 24 at the second set pressure value.

It should be noted that, after these processings, negative pressure adjusting control AdjV2 is carried out in Step S80. This control is effected in order to set a negative pressure required during the subsequent contraction period in the tank 42 while the balloon pump 33 is held in the contracted state by means of the negative pressure. Since this control is the same as that explained with reference to the flow chart shown in FIG. 5, description thereof is omitted.

Figure 8:
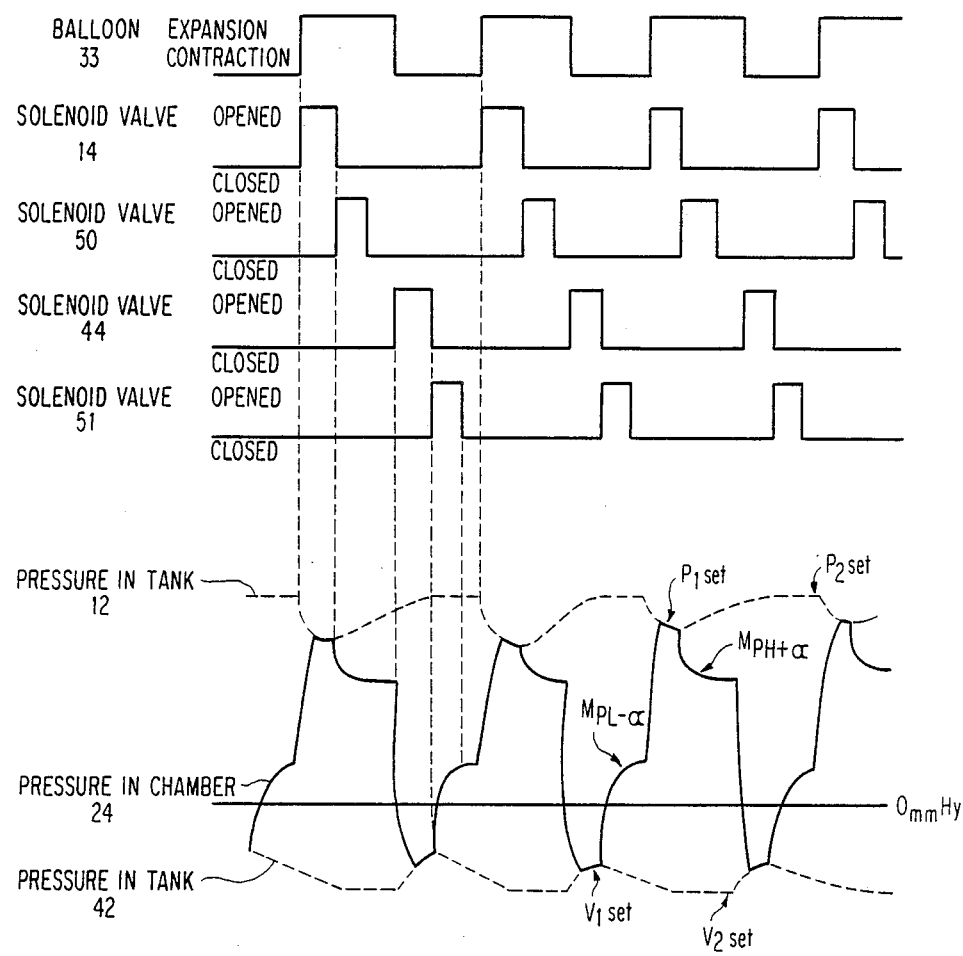
FIG. 8 is a timing chart showing the operation of the embodiment.

FIG. 8 is a chart showing the timing at which each of the solenoid valves is opened or closed. The operation of this embodiment will be summed up below with reference to this timing chart.

(i) Expansion period of the balloon pump 33:

1. When the solenoid valve 14 is opened, a positive pressure having a set positive pressure value P2set which is set in the tank 12 is supplied to the input chamber 24 of the isolator 20, thus causing the plate 27 to move. At this time, the pressure in the tank 12 lowers. The pressure regulating valve 11 is activated so that the pressure in the tank 12 is adjusted to a pressure value P1set which is appropriate to drive the plate 27.

At the same time, the pressure in the vacuum tank 42 is set in advance to a pressure value V2set which is required at the beginning of the subsequent contraction period.

2. When the plate 27 reaches the predetermined position STset1 during the expansion period, the solenoid valve 14 is closed, while the solenoid valve 50 is opened. Thus, the pressure in the input chamber 24 is lowered to a pressure value $Mph+\alpha$ at which the balloon pump 33 can be held in the expanded state. This pressure value is set so as to be higher than the highest blood pressure value of a living organism under treatment.

When the pressure in the input chamber 24 reaches the set value $Mph+\alpha$, the solenoid valve 50 is closed to hold this pressure level until the subsequent contraction of the pump 33 begins.

At the same time, the pressure inside the positive pressure tank 12 the supply of which has already been cut off by means of the solenoid valve 14 is set in advance at the pressure value P2set which is required at the beginning of the subsequent expansion period.

(ii) Contraction period of the balloon pump 33:

1. The solenoid valve 44 is first opened. In consequence, the input chamber 24 of the isolator 20 is supplied with a negative pressure having a negative pressure value V2set which is set in the tank 42, thus causing the plate 27 to move. At this time, the pressure in the tank 42 rises. Further, the pressure regulating valve 41 is activated so that the pressure in the tank 42 is adjusted to a pressure value V1set which is appropriate to drive the plate 27.

At the same time, the pressure in the positive pressure tank 12 is set in advance to a pressure value P2set which is required at the beginning of the subsequent expansion period.

2. When the plate 27 reaches the predetermined position STset0 during the contraction period, the solenoid valves 44 and 51 are closed and opened, respectively, to raise the pressure in the input chamber 24 to a pressure value $Mpl-\alpha$ at which the balloon pump 33 can be maintained in the contracted state. This pressure value is set so as to be lower than the lowest blood pressure value of the living organism under treatment.

When the pressure in the input chamber 24 reaches the set value $Mpl-\alpha$, the solenoid valve 51 is closed to hold this pressure until the subsequent expansion of the pump 33 begins.

At the same time, the pressure inside the negative pressure tank 42 the supply of which has already been cut off by means of the solenoid valve 44 is set in advance at the pressure value V2set which is required at the beginning of the subsequent contraction period.

It should be noted that the relationship between the various set values is as follows. (Set positive pressure values)

$$0 < Mph+\alpha < P1set < P2set$$

(Set negative pressure values)
$$V2set < V1set < 0 < Mpl-\alpha < Mph+\alpha$$

As has been described above, according to the present invention, after the movable membrane has been moved to a predetermined position during the expansion period, the positive pressure is lowered to a level at which the movable membrane can satisfactorily be held at said position. Accordingly, when a negative pressure is supplied by opening the second switching valve means at the subsequent timing, the negative pressure can be made to act even more effectively. In other words, it is possible to quicken the movement of the medical appliance when contracted.

In addition, when the medical appliance is expanded, it is possible to supply a pressure medium having a pressure which is higher than that in the case of the conventional driving apparatuses. This is because, after the movable membrane has moved to a predetermined position, the pressure is lowered to a level at which the movable membrane can satisfactorily be held at said position, whereby it is possible to prevent application of an excessively high pressure to the medical appliance. Accordingly, it is possible to quicken the movement of the medical appliance when expanded.

During the contraction period, after the movable membrane has been moved to a predetermined position, the negative pressure is raised to a level at which the movable membrane can satifactorily be held at said position. Accordingly, when a positive pressure is supplied by switching the switching valve means at the subsequent timing, the positive pressure can be made to act even more effectively. In other words, it is possible to quicken the movement of the medical appliance when expanded.

In this case also, when the medical appliance is to be contracted, it is possible to supply a pressure medium which has a lower pressure than that in the case of the conventional driving apparatuses. Accordingly, it is possible to quicken the movement of the medical appliance when contracted.

Although the present invention has been described through specific terms, it should be noted here that the described embodiment is not necessarily limitative and various changes and modifications may be imparted thereto without departing from the scope of the invention which is limited solely by the appended claims.

What is claimed is:

1. A medical appliance driving apparatus comprising:
   positive pressure supply means for supplying a positive pressure:
   negative pressure supply means for supplying a negative pressure;
   isolator means for separating a fluid in each of said supply means from a fluid in said medical appliance, said isolator means having a housing including an input chamber and an output chamber separated by movable membrane means with the medical appliance connected to the output chamber;
   first switching valve means connected to said positive pressure supply means and having its output side connected to said input chamber of said isolator means;
   second switching valve means connected to said negative pressure supply means and having its input side connected to said input chamber of said isolator means;
   additional valve means connected to said input chamber of said isolator means and the atmosphere;
   pressure detecting means for detecting the pressure in said input chamber of said isolator means;
   position detecting means for detecting the position of said membrane means in said isolator means;
   electronic control means connected to said first and second switching valve means, said additional valve means, said position detecting means and said pressure detecting means,
   said electronic control means opens said first switching valve means, closes said second switching valve means and closes said additional valve means for supplying said input chamber with a positive pressure, closes said first switching valve means, opens said second switching valve means and closes said additional valve means for supplying said input chamber with a negative pressure and repeats the foregoing sequence,
   said electronic control means opens said additional valve means when said position detecting means detects said membrane means at a predetermined limit position and when the pressure valve detected by said pressure detecting means is larger than a predetermined pressure value at a time when both of said first switching valve means and said second switching valve means are closed subsequent to the closing of said first switching valve means after supplying positive pressure to said input chamber,
   said pressure value being larger than the highest blood pressure value of a patient to whom the medical appliance is adapted to be connected and smaller than a pressure value in said input chamber at the time said first switching valve means is opened.

2. A medical appliance driving apparatus comprising:
   positive pressure supply means for supplying a positive pressure;
   negative pressure supply means for supplying a negative pressure;
   isolator means for separating a fluid in each of said supply means from a fluid in said medical appliance, said isolator means having a housing including an input chamber and an output chamber separated by movable membrane means with the medical appliance connected to the output chamber;
   first switching valve means connected to said positive pressure supply means and having its output side connected to said input chamber of said isolator means;
   second switching valve means connected to said negative pressure supply means and having its input side connected to said input chamber of said isolator means;
   additional valve means connected to said input chamber of said isolator means and said positive pressure supply means;
   pressure detecting means for detecting the pressure in said input chamber of said isolator means;
   position detecting means for detecting the position of said membrane means in said isolator means;
   electronic control means connected to said first and second switching valve means, said additional valve means, said position detecting means and said pressure detecting means,
   said electronic control means opens said first switching valve means, closes said second switching valve means and closes said additional valve means for supplying said input chamber with a positive pressure, closes said first switching valve means, opens said second valve means and closes said additional valve means for supplying said input chamber with a negative pressure and repeats the foregoing sequence,
   said electronic control means opens said additional valve means when said position detecting means detects said membrane means at a predetermined limit position and when the pressure value detected by said pressure deteting means is larger than a predetermined pressure value at a time when both of said first switching valve means and said second switching valve means are closed subsequent to the closing of said second switching valve means after supplying negative pressure to said input chamber, said predetermined pressure value being smaller than the lowest blood pressure value of a patient to whom the medical appliance is adapted to be connected and larger than a pressure value in said input chamber at the time that said second switching valve means is opened.

3. A medical appliance driving apparatus comprising:

positive pressure supply means for supplying a positive pressure;

negative pressure supply means for supplying a negative pressure;

isolator means for separating a fluid in each of said supply means from a fluid in said medical appliance, said isolator means having a housing including an input chamber and an output chamber separated by movable membrane means with the medical appliance connected to the output chamber;

first switching valve means connected to said positive pressure supply means and having its output side connected to said input chamber of said isolator means;

second switching valve means connected to said negative pressure supply means and having its input side connected to said input chamber of said isolator means;

third valve means connected to said input chamber of said isolator means and the atmosphere;

fourth valve means connected to said input chamber of said isolator means and said positive pressure supply means;

pressure detecting means for detecting the pressure in said input chamber of said isolator means;

position detecting means for detecting the limit positions of said movable membrane means in said isolator means; and electronic control means connected to said first and second switching valve means, said third valve means, said fourth valve means, said position detecting means and said pressure detecting means, said electronic control means, first, opens said first switching valve means and closes said second switching valve means, second, closes said first switching means when the detected position of said movable membrane means is in a first limit position, third, opens said third valve means when the pressure value detected by said pressure detecting means is larger than a first predetermined pressure value and closes said third valve means when the pressure equals the first predetermined pressure value, fourth, closes said first switching valve means and open said second switching valve means, fifth, closes said second pressure valve means when the detected position of said movable membrane is in a second limit position, sixth, opens said fourth valve means when the detecting pressure value of said pressure deteting means is smaller than a second predetermined pressure value, closes said fourth valve means when the pressure equals said second predetermined pressure value and repeats the foregoing sequence, said first predetermined pressure value is larger than the highest blood pressure value of a patient to whom said medical appliance is adapted to be connected and smaller than a pressure value in said input chamber, at the time that said first switching valve means is opened, said second predetermined pressure value is smaller than the lowest blood pressure value of said patient and larger than a pressure value in said input chamber at the time that said second switching valve means is opened.

* * * * *